United States Patent [19]

Miura

[11] Patent Number: 5,815,607
[45] Date of Patent: Sep. 29, 1998

[54] IMAGE READING DEVICE, AND INSPECTION APPARATUS AND EXPOSURE APPARATUS USING THE DEVICE

[75] Inventor: Seiya Miura, Utsunomiya, Japan

[73] Assignee: Canon Kabushiki Kaisha, Tokyo, Japan

[21] Appl. No.: 734,846

[22] Filed: Oct. 22, 1996

Related U.S. Application Data

[63] Continuation of Ser. No. 275,276, Jul. 15, 1994, abandoned.

[30] Foreign Application Priority Data

Jul. 19, 1993 [JP] Japan .................. 5-178154

[51] Int. Cl.⁶ ............................................. G06K 9/00
[52] U.S. Cl. ................................... 382/275; 382/321
[58] Field of Search ..................... 348/246, 247,
348/251, 92; 382/144, 149, 309, 112, 113,
135, 137, 138, 167, 254, 255, 256, 257,
258, 259, 260, 266, 267, 268, 269, 270,
274, 275, 282, 283, 300, 307, 308, 312,
321, 317, 318, 322, 323, 324; 358/482,
471, 505, 509; 359/654

[56] References Cited

U.S. PATENT DOCUMENTS

| | | | |
|---|---|---|---|
| 4,366,500 | 12/1982 | Kurtz et al. | 358/75 |
| 4,399,464 | 8/1983 | Hix et al. | 348/246 |
| 4,488,178 | 12/1984 | Koslov et al. | 348/246 |
| 4,600,946 | 7/1986 | Levine | 348/246 |
| 4,701,032 | 10/1987 | Takada | 350/413 |
| 4,701,784 | 10/1987 | Matsuoka et al. | 348/251 |
| 4,748,507 | 5/1988 | Gural | 348/246 |
| 4,783,700 | 11/1988 | Nagane | 358/213.11 |
| 5,058,177 | 10/1991 | Chemaly | 382/149 |
| 5,248,876 | 9/1993 | Kerstens et al. | 250/561 |
| 5,294,993 | 3/1994 | Sable | 358/350 |

*Primary Examiner*—Leo H. Boudreau
*Assistant Examiner*—Bijan Tadayon
*Attorney, Agent, or Firm*—Fitzpatrick, Cella, Harper & Scinto

[57] ABSTRACT

An image reading device for detecting a foreign object on a substrate includes a lens array for forming an erect image of the object in response to the foreign object being illuminated by a light source, and a sensor array for reading the formed image of the object. The sensor array includes a plurality of pixels, with at least some of the pixels having a dead zone. The lens array and the sensor array are arranged such that the substrate and the photosensing surface of the sensor array are situated at positions separated by substantially the same distance from two conjugate points present when the lens array forms the erect image of the object. The arrangement results in the image being defocused on the sensor array such that a predetermined number of pixels sense the formed image of the object, thus assuring that the foreign object is detected even if the image is projected on a dead zone of a given pixel.

9 Claims, 9 Drawing Sheets

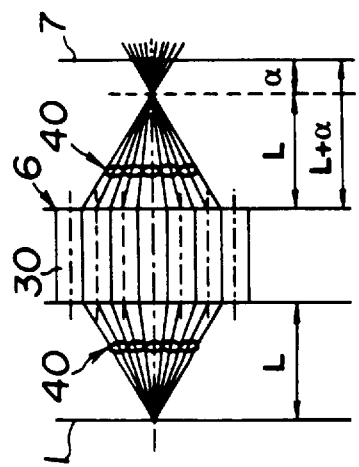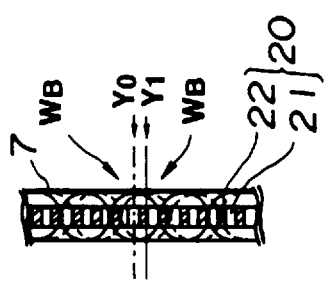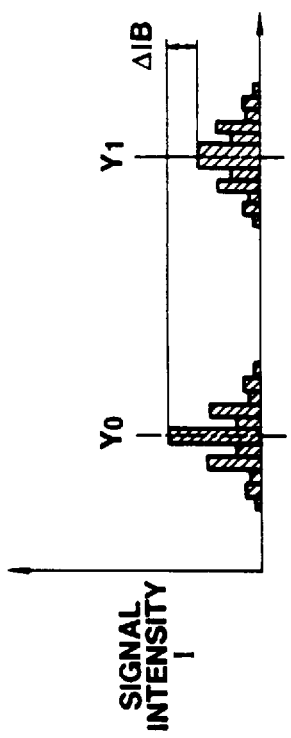
FIG.3(B)-1  FIG.3(B)-2  FIG.3(B)-3

IMAGE READING DEVICE, AND INSPECTION APPARATUS AND EXPOSURE APPARATUS USING THE DEVICE

This application is a continuation of application Ser. No. 08/275,276 filed Jul. 15, 1994, now abandoned.

BACKGROUND OF THE INVENTION

1. Field of the Invention

This invention relates to an image reading device, to a surface-state inspection apparatus and to an exposure apparatus which includes the surface-state inspection apparatus. The surface-state inspection apparatus precisely detects the presence and the position of foreign matter on the surface of a substrate, such as a reticle, a photomask or the like having a circuit pattern formed thereon, and/or the surface of a pellicle for preventing adherence of foreign matter to the substrate on which the pellicle is mounted. The surface-state inspection apparatus is used by being incorporated in an exposure apparatus for manufacturing semiconductor devices, such as IC's (Integrated Circuits), LSI's (Large-Scale Integrated Circuits) and the like, and other devices such as CCD's (Charge Coupled Devices), liquid-crystal panels, magnetic heads and the like.

2. Description of the Related Art

In the process of manufacturing IC's and LSI's, in general, a circuit pattern formed on a substrate, such as a reticle, a photomask or the like, is transferred onto a wafer, on which a resist is coated, using an exposure apparatus (a stepper or a mask aligner).

In this transfer process, if foreign matter, such as a pattern defect, a dust particle or the like, is present on the surface of the substrate, the foreign matter is also transferred onto the wafer, thereby causing a decrease in the production yield in the manufacture of IC's and LSI's.

Particularly when a circuit pattern on a reticle is repeatedly printed onto a plurality of shot regions on a wafer by a step-and-repeat method, if a single harmful foreign matter is present on the reticle, the foreign matter is printed onto the respective shot regions on the entire surface of the wafer, thereby causing a significant decrease in the production yield in the manufacture of IC's and LSI's.

Accordingly, it is indispensable to detect the presence of foreign matter on a substrate in the process of manufacturing IC's and LSI's. In general, an inspection method utilizing the property of foreign matter to isotropically scatter light is adopted.

For example, a surface is inspected by obliquely projecting from above a parallel light beam onto the surface, and condensing scattered light from foreign matter onto a one-dimensional image sensor array by a refractive-index-distribution-type microlens array to image the foreign matter.

When viewing the entire surface to be inspected with unit magnification, it is necessary to provide a one-dimensional image sensor whose effective pixel (picture element) range equals at least the inspection region of the surface. In general, as shown in FIG. 4, such a long one-dimensional image sensor includes a plurality of pixels 20, with each such pixel having a photosensitive portion 21 and in most cases a dead zone 22. Each pixel 20 has a size of about 60–70 μm, and the dead zone 22 has a size of about 20–30 μm. The use of a one-dimensional image sensor not having dead zones causes an increase in the cost of an inspection apparatus. Hence, in order to provide a simple and inexpensive inspection apparatus, it is necessary to use the above-described one-dimensional image sensor having dead zones.

When the above-described one-dimensional image sensor having dead zones is provided at the best imaging position of the refractive-index-distribution-type microlens array, if scattered light from foreign matter is imaged onto a dead zone, a sufficient signal for detecting foreign matter cannot be obtained. Accordingly, the presence of foreign matter may not be detected depending on the location of the foreign matter.

SUMMARY OF THE INVENTION

The present invention has been made in consideration of the above-described problems.

It is an object of the present invention to provide an improved apparatus.

It is still another object of the present invention to provide an image reading device, a surface-state inspection apparatus, and an exposure apparatus which includes the surface-state inspection apparatus, in which the presence of foreign matter is detected.

According to one aspect, the present invention which achieves these objectives relates to an image reading device for reading an image of an object, formed by a lens array for forming an erect image, by a sensor array having a dead zone for each pixel in the array, wherein the lens array and the sensor array are disposed so that the object and the photosensing surface of the sensor array are situated at positions separated by substantially the same distance from two conjugate points (an object point and an image point) present when the lens array forms an erect image having unit magnification.

According to another aspect, the present invention which achieves these objectives relates to a surface-state inspection apparatus for inspecting a surface state of a surface by projecting an image of the surface formed by a lens array for forming an erect image onto a sensor array having a dead zone for each pixel in the array, and using an output from the sensor array, wherein the lens array and the sensor array are disposed so that the surface and the photosensing surface of the sensor array are situated at positions separated by substantially the same distance from two conjugate points (an object point and an image point) present when the lens array forms an errect image having unit magnification.

The surface-state inspection apparatus of the present invention is used by being incorporated in an exposure apparatus for manufacturing semiconductor devices, such as IC's, LSI's and the like, and various kinds of other devices, such as CCD's, liquid-crystal panels, magnetic heads and the like, or is used by itself.

By inspecting for the presence of forein matter on a reticle for manufacturing devices or on a pellicle for protecting the reticle from foreign matter using the surface-state inspection apparatus of the present invention, foreign matter is detected, thereby causing an increase in the production yield in the manufacure of devices.

The foregoing and other objects, advantages and features of the present invention will become more apparent from the following description of the preferred embodiments taken in conjunction with the accompanying drawings.

BRIEF DESCRIPTION OF THE DRAWINGS

FIGS. 3(A) through 3(C) are diagrams illustrating light-condensing states on the photosensing surface of a one-dimensional image sensor at different imaged states, and signal outputs obtained from the one-dimensional image sensor;

DESCRIPTION OF THE PREFERRED EMBODIMENTS

Figure 1A:
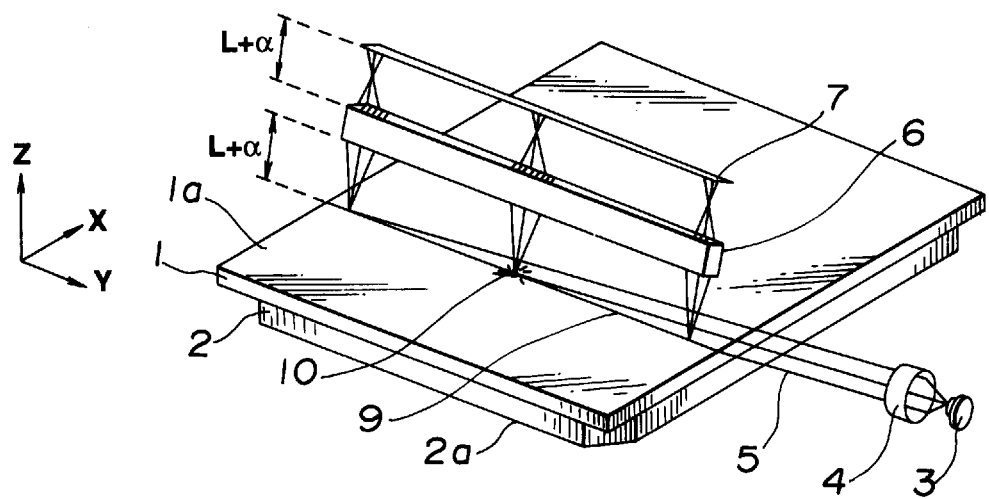
FIGS. 1(A) and 1(B) are schematic diagrams illustrating an embodiment of the present invention.
Figure 1B:
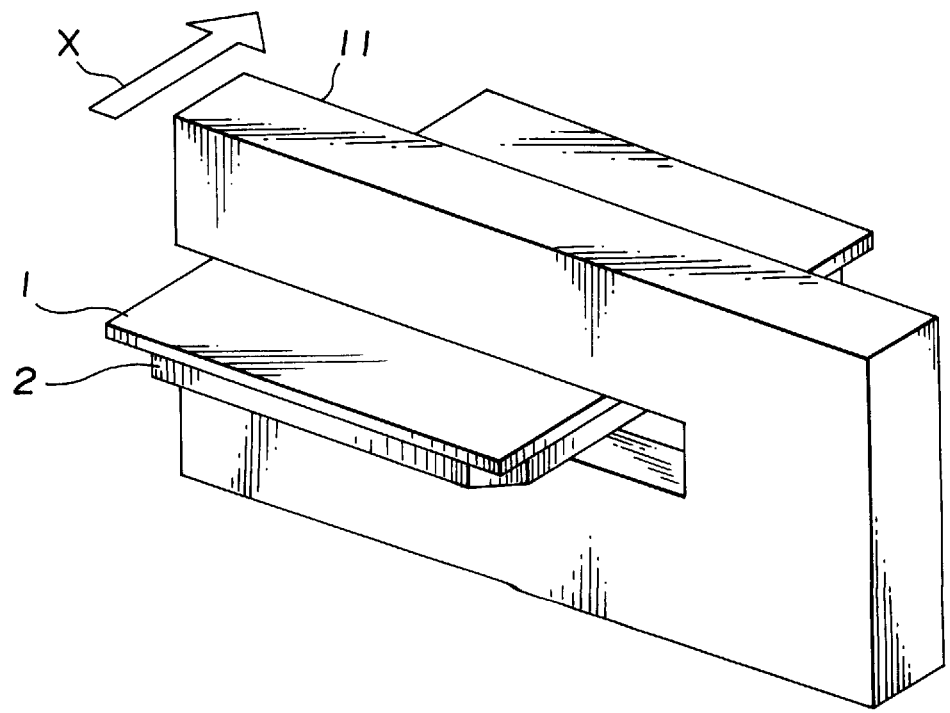

FIGS. 1(A) and 1(B) are schematic diagrams illustrating an embodiment of the present invention. FIG. 1(A) illustrates an optical system, and FIG. 1(B) illustrates an external appearance of the optical system. In FIG. 1(A), in order to simplify the description, only an optical system at the back (a blank surface) of a reticle 1 is shown. However, the device of the present embodiment also includes an optical system for inspecting foreign matter on the surface (a chromium surface) of the reticle 1 and on a pellicle 2a attached to a pellicle frame 2.

A laser beam 5 having a spread angle is emitted from a semiconductor laser 3, and is converted into a parallel light beam by a collimating lens 4. The parallel laser beam 5 is projected onto, and substantially parallel with, a blank surface 1a of the reticle 1, serving as a surface to be inspected.

Thus, a linear laser-beam-illuminated region 9 extending in the Y direction is formed on the blank surface 1a.

If foreign matter 10 is present on the laser-beam-illuminated region 9, scattered light is generated from the foreign matter 10. The scattered light is condensed onto the neighborhood of a one-dimensional image sensor 7 by a refractive-index-distribution-type microlens array (hereinafter termed a "lens array") 6 disposed along the laser-beam-illuminated region 9, and the foreign matter 10 is imaged on that portion.

As shown in FIG. 1(A), the lens array 6 and the one-dimensional image sensor 7 are disposed such that the one-dimensional image sensor 7 is defocused backward from the best imaged position L of the lens array 6 by a distance α while maintaining the front-side focal length (the distance between the blank surface 1a and the lens array 6) and the rear-side focal length (the distance between the lens array 6 and the photosensing surface of the sensor 7) at an equal value of L+α.

As shown in FIG. 1(B), in the apparatus of the present embodiment, by linearly moving the entire optical system 11 in a direction (the X direction) perpendicular to the longitudinal direction, i.e., the direction of arrangement, of the one-dimensional image sensor 7 to scan the blank surface 1a, and discriminaing the level of an output from the one-dimensional image sensor 7, the entire surface of the reticle 1 is inspected.

The entire optical system 11 is driven by a driving device (not shown). The apparatus may be configured such that the reticle 1 is moved in the X direction instead of moving the entire optical system 11. The arrangement of the lens array 6 and the one-dimensional image sensor 7 will now be described in detail.

Figure 2C:
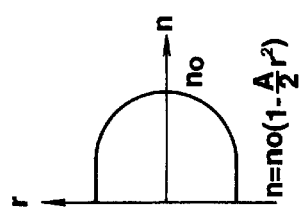
FIGS. 2(A) through 2(C) are diagrams illustrating imaging characteristics of a single refractive-index-distribution-type microlens.
Figure 2A:
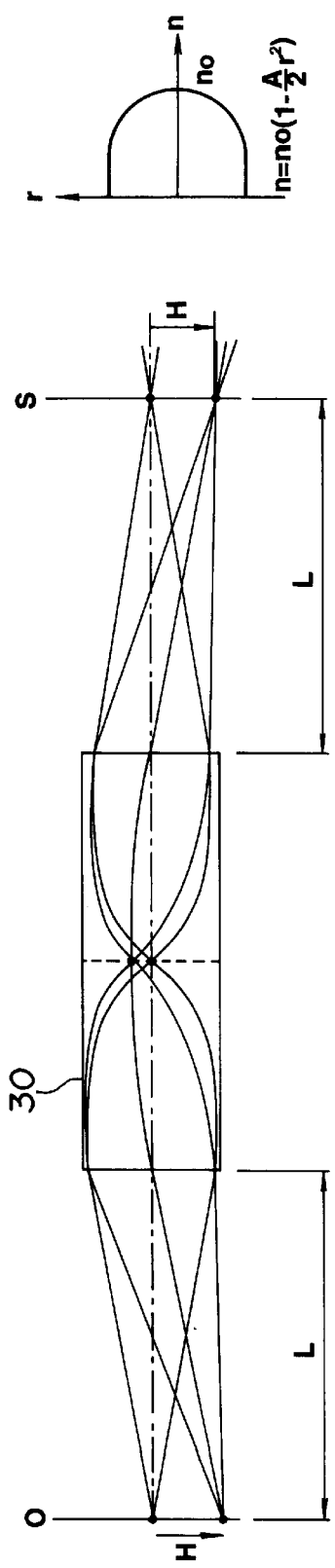
Figure 2B:
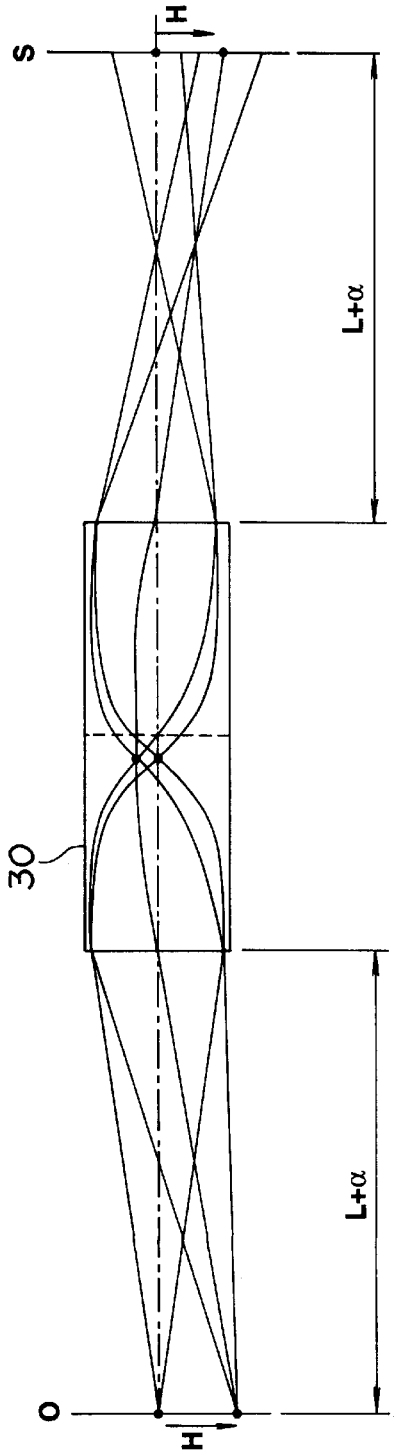

FIGS. 2(A) through 2(C) are diagrams illustrating imaging characteristics of a single refractive-index-distribution-type microlens 30 of the lens array 6. The lens 30 has the refractive-index distribution shown in FIG. 2(C) in the direction of the radius r, and condenses, as shown in FIG. 2(A), an incident light beam onto one point so that an erect image having unit magnification is formed on an image plane S. When the sensor 7 is defocused while maintaining the distance of the object and the distance of the image plane with respect to the lens 30 at L+α, only the condensed state (image) has a defocused state while maintaining the condition of an erect image having unit magnification on the image plane S, as shown in FIG. 2(B). Since the lens array 6 comprises a plurality of refractive-index-distribution-type microlenses 30 each having the above-described characteristics, imaged states by the lens array 6 become as shown in FIGS. 3(A) through 3(C).

Figures 3, 3A:
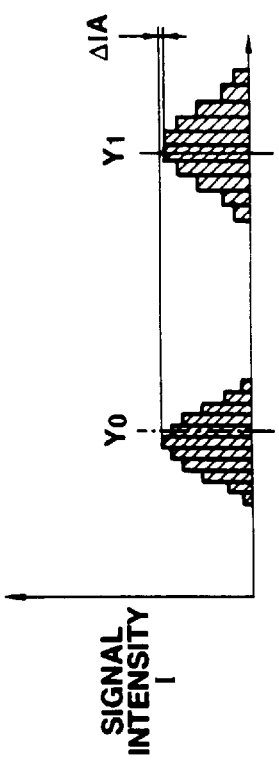
Figures 2, 3A:
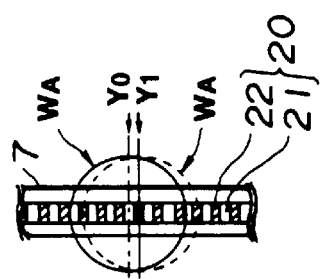
Figures 1, 3A:
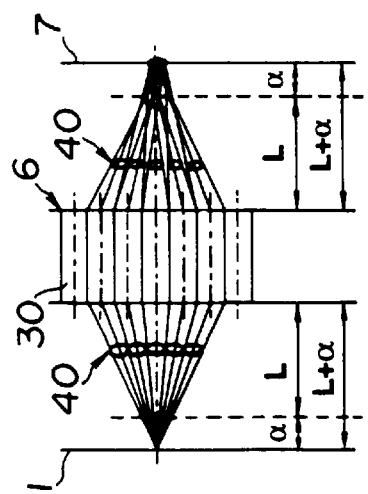
Figures 1, 3C:
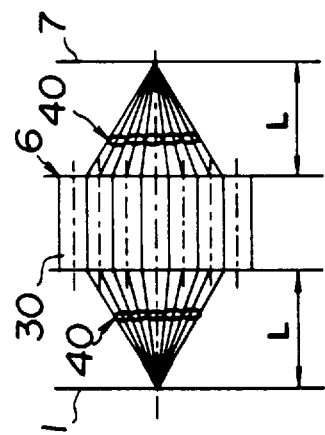
Figures 2, 3C:
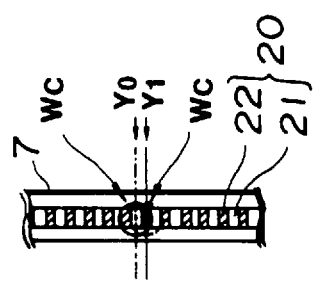
Figures 3, 3C:
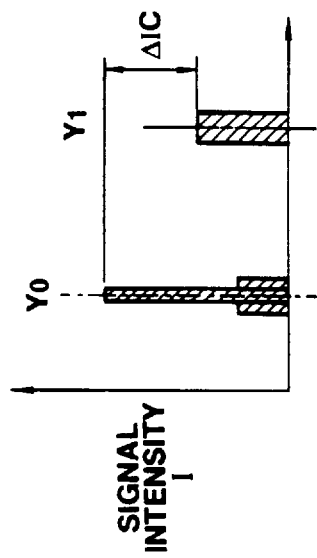
Figure 4:
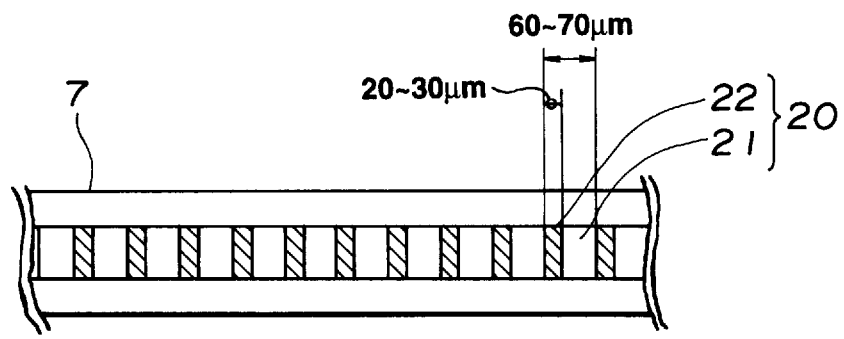
FIG. 4 is a diagram illustrating dead zones in a one-dimensional image sensor.

FIGS. 3(A) through 3(C) illustrate light-condensing states on the one-dimensional image sensor 7 in different imaged states, and signals obtained from the image sensor 7. For the purpose of easy understanding, imaged states when the lens array 6 is defocused are illustrated. FIG. 3(A) illustrates an imaged state in the present embodiment. FIG. 3(B) illustrates an imaged state when only the one-dimensional image sensor 7 is defocused. FIG. 3(C) illustrates an imaged state in a conventional case.

In the imaged state shown in FIG. 3(C), the spot size $\omega_C$ on the one-dimensional image sensor 7 is about 100 μm. When the pitch of pixels 20 in the long one-dimensional image sensor 7 is about 60–70 μm and the width of a dead zone 22 is about 20–30 μm, since a signal cannot be obtained from the region of a dead zone 22, the intensity ($Y_0$) of a signal output when the light beam is condensed onto the center of a photosensitive portion 21 of a pixel is about twice the intensity ($Y_1$) of a signal output when the light beam is condensed onto the center of the dead zone 22.

When only the one-dimensional image sensor 7 is defocused by a distance α as shown in FIG. 3(B), a disordered light-condensing state is obtained, because the light-condensing position of each microlens 30 differs on the one-dimensional image sensor 7. Hence, the signal output from the one-dimensional image sensor 7 is unstable, and variations in the intensity of the signal are produced depending on the location.

On the other hand, in the present embodiment, as shown in FIG. 3(A), when the reticle 1 and the one-dimensional image sensor 7 are defocused with respect to the lens array 6 while maintaining both the distance of the object point and the distance of the image plane at L+α, the light-condensing point of each microlens 30 is in front of the photosensing surface of the sensor 7, but principal rays from respective microlenses 30 are condensed on substantially the same point on the photosensing surface of the sensor 7. That is, since defocused light beams from respective microlenses 30 are condensed onto sustantially the same point, a single suffiently spread spot size $\omega_A$ is formed. As a result, the signal output from the sensor 7 is stable irrespective of the light-condensing position on the sensor 7.

If the amount of defocus α is selected so that in the neighborhood of 7, 9–10 pixels of the sensor 7 are included within the spot size $\omega_A$, the influence of the dead zone can be considerably reduced.

Figure 5:
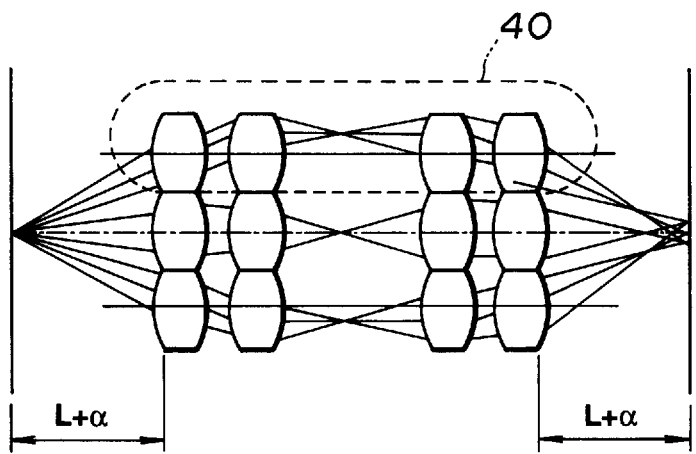
FIG. 5 is another example of a lens array using errect lenses having unit magnification.

In the present invention, the same effects may also be obtained in the case of a lens array comprising a plurality of two-dimensionally arranged refractive-index-distribution-type microlenses. Although a description has been provided of the case in which the refractive-index-distribution-type microlenses are used for the lens array, a lens array, comprising, as shown in FIG. 5, a plurality of erect lenses 40 having unit magnification, each comprising four homogeneous lens elements, may also be used.

Figure 6:
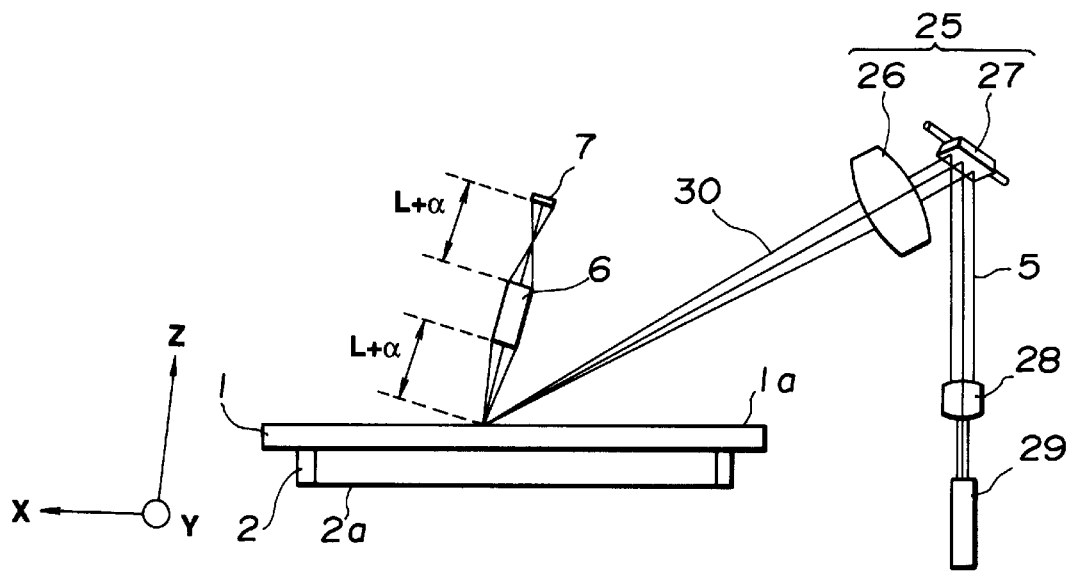
FIG. 6 is a diagram illustrating another embodiment of the present invention.

FIG. 6 illustrates another embodiment of the present invention. The configuration and the arrangement of a lens array 6 and a one-dimensional image sensor 7 in the present embodiment are the same as in the above-described embodiment. In the above-described embodiment, the laser beam is made into a parallel light beam when projecting it onto the reticle 1. However, the same effect may also be obtained in the present embodiment, in which the surface of a blank surface 1a, serving as a surface to be inspected, is linearly scanned with a condensed light beam 30 using optical scanning means 25. In FIG. 6, there are also shown a scanning lens 26 comprising an f-θ lens and the like, light-deflecting means 27, such as a galvanomirror, a polygonal mirror or the like, a beam expander 28, and a laser light source 29.

The above-described foreign-matter inspection apparatus can be used by being incorporated in an exposure apparatus for manufacturing semiconductor devices, such as IC's, LSI's and the like, and various kinds of other devices, such as CCD's, liquid-crystal panels, magnetic heads and the like, or can be used by itself.

Figure 7:
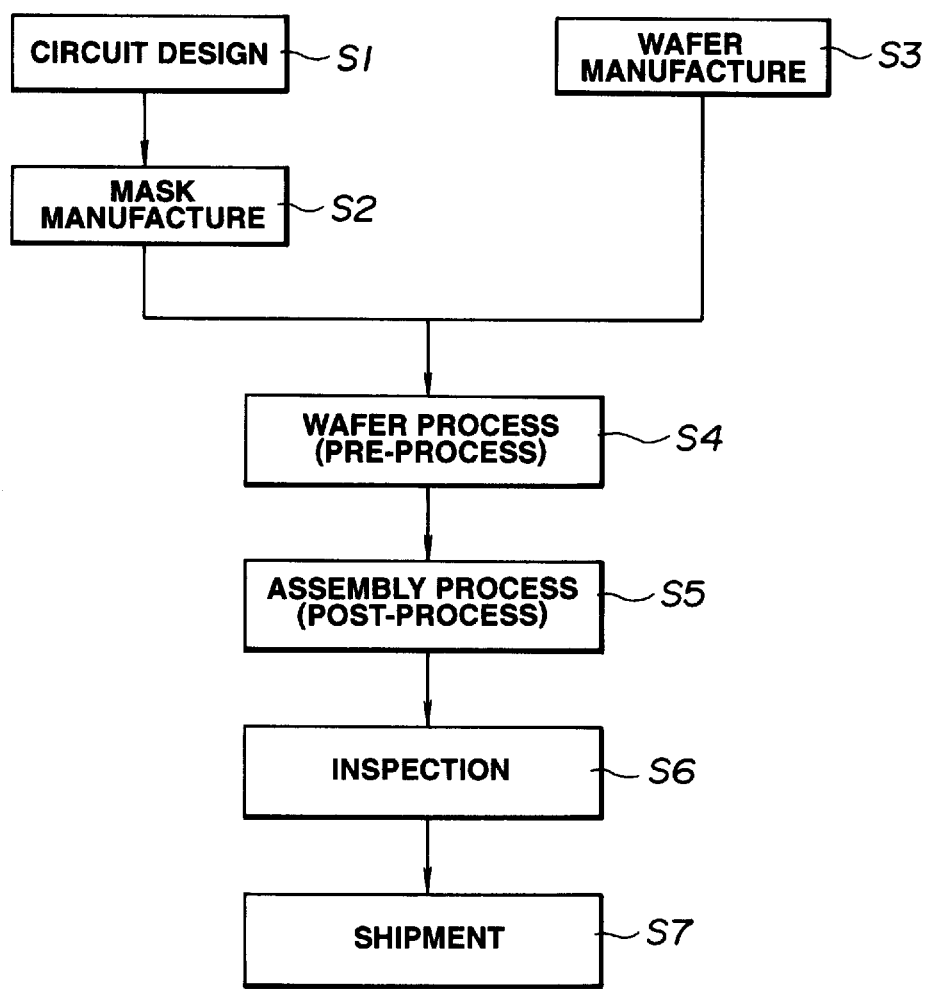
FIG. 7 is a flow diagram illustrating the production flow of semiconductor devices.

Next, a description is provided of a device manufacturing method utilizing the above-described exposure apparatus. FIG. 7 shows a flow diagram for manufacturing semiconductor devices, such as IC's, LSI's and the like, and various kinds of other devices, such as liquid-crystal panels, CCD's, and the like. In step S1 (circuit design), circuit design of semiconductor devices is performed. In step S2 (mask manufacture), masks, on which designed circuit patterns are formed, are manufactured. In step S3 (wafer manufacture), wafers are manufactured using a material, such as silicon or the like. Step S4 (wafer process) is called a preprocess, in which actual circuits are formed on the wafers by means of photolithography using the above-described masks and wafers. The next step S5 (assembly process) is called a postprocess which manufactures semiconductor chips using the wafers manufactured in step S4, and includes an assembling process (dicing and bonding), a packaging process (chip encapsulation), and the like. In step S6 (inspection), inspection operations, such as operation-confirming tests, durability tests, and the like of the semiconductor devices manufactured in step S5, are performed. The manufacture of semiconductor devices is completed after passing through the above-described processes, and the manufactured devices are shipped (step S7).

Figure 8:
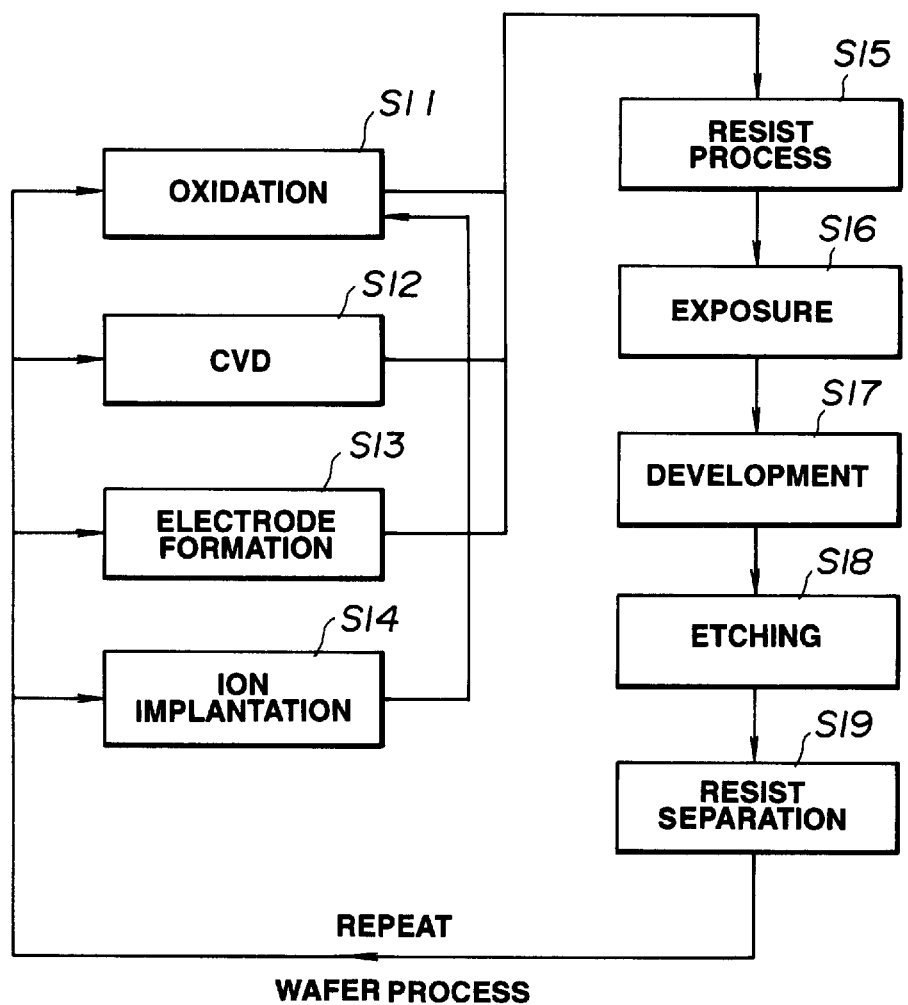
FIG. 8 is a flow diagram illustrating the wafer process shown in FIG. 7.

FIG. 8 shows the detailed flow diagram of the above-described wafer process. In step S11 (oxidation), the surface of the wafer is oxidized. In step S12 (CVD), an insulating film is formed on the surface of the wafer. In step S13 (electrode formation), electrodes are formed on the surface of the wafer by vacuum deposition. In step S14 (ion implantation), ions are implanted into the wafer. In step S15 (resist process), a photosensitive material is coated on the wafer. In step S16 (exposure), the circuit pattern on the mask after being inspected using the foreign-matter inspection apparatus of the present invention is exposed and printed on the wafer by the above-described exposure apparatus. In step S17 (development), the exposed wafer is developed. In step S18 (etching), portions other than the developed resist image are etched off. In step S19 (resist separation), the resist which becomes unnecessary after the completion of the etching is removed. By repeating these steps, a final circuit pattern made of multiple patterns is formed on the wafer.

The individual components shown in outline in the drawings are all well known in the image reading device, inspection apparatus and exposure apparatus arts and their specific contruction and operation are not critical to the operation or the best mode for carrying out the invention.

While the present invention has been described with respect to what is presently considered to be the preferred embodiments, it is to be understood that the invention is not limited to the disclosed embodiments. To the contrary, the present invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A surface inspection device, comprising:

a lens array for forming an image of a surface to be inspected;

a sensor array for reading the formed image, with the sensor array including a plurality of pixels, with at least some of the pixels including a dead zone, wherein said lens array and said sensor array are disposed so that the surface to be inspected is situated at a position separated by a predetermined distance (α) which is not zero from one of two opposed conjugate points of said lens array and the photosensing surface of said sensor array is situated at a position separated by the predetermined distance (α) from another one of the two opposed conjugate points of said lens array, such that defocused light beams from respective lenses of said lens array are condensed onto substantially the same point on the photosensing surface to cover an area of at least 9 pixels of said sensor array, so as to compensate for the dead zone of said sensor array; and means for inspecting the surface to be inspected based on an output from said sensor array.

2. A device according to claim 1, wherein said lens array comprises refractive-index-distribution-type microlenses.

3. A device according to claim 1, further comprising means for illuminating the surface to be inspected with a parallel light beam from a direction substantially parallel to the surface.

4. A device according to claim 1, further comprising scanning means for condensing a light beam onto the surface to be inspected, and for moving the light beam on the surface.

5. A device according to claim 1, wherein said sensor array comprises a one-dimensional sensor array, and further comprising means for moving said lens array and said sensor array in a direction crossing the longitudinal direction of said sensor array.

6. A device according to claim 1, wherein said surface is a reticle surface or a pellicle surface, and wherein foreign matter on the surface is detected.

7. A surface inspection apparatus for inspecting a surface to be inspected, comprising;

a lens array for forming an image of the surface to be inspected; and a sensor array for reading the formed image, with the sensor array including a plurality of pixels, an output from said sensor array being used for inspecting the surface to be inspected, wherein said lens array and said sensor array are disposed so that defocused light beams from respective lenses of said lens array receiving light from the surface to be inspected are condensed onto substantially the same point on a photosensing surface of said sensor array.

8. An apparatus according to claim 7, wherein said surface to be inspected is a reticle surface or a pellicle surface.

9. An apparatus according to claim 7, wherein said lens array comprises refractive-index-distribution-type microlenses.

* * * * *

UNITED STATES PATENT AND TRADEMARK OFFICE
CERTIFICATE OF CORRECTION

PATENT NO. : 5,815,607
DATED : September 29, 1998
INVENTOR(S) : SEIYA MIURA

It is certified that error appears in the above-identified patent and that said Letters Patent is hereby corrected as shown below:

COLUMN 2

Line 32, "errect" should read --erect--.
Line 39, "errect" should read --erect--.
Line 46, "forein" should read --foreign--.

COLUMN 3

Line 53, "discriminaing" should read --discriminating--.

Signed and Sealed this

Fifteenth Day of June, 1999

Attest:

Q. TODD DICKINSON

Attesting Officer  Acting Commissioner of Patents and Trademarks